United States Patent
Harris (10) Patent No.: US 7,242,318 B2
(45) Date of Patent: Jul. 10, 2007

(54) EVENT DETECTION AND TRANSMISSION SYSTEM

(75) Inventor: Alan Harris, Amersham (GB)

(73) Assignee: Accenture Global Services GmbH, Schaffhausen (CH)

( * ) Notice: Subject to any disclaimer, the term of this patent is extended or adjusted under 35 U.S.C. 154(b) by 270 days.

(21) Appl. No.: 10/769,206

(22) Filed: Jan. 29, 2004

(65) Prior Publication Data

US 2004/0183675 A1    Sep. 23, 2004

(30) Foreign Application Priority Data

Jan. 30, 2003    (EP)    ................................. 03250577

(51) Int. Cl.
*H04Q 9/00* (2006.01)

(52) U.S. Cl. .................. 340/870.07; 340/539.13; 340/870.16; 340/309.16; 340/568; 700/12; 700/52; 700/53; 700/65; 600/300; 600/483; 128/903; 128/904

(58) Field of Classification Search ........... 340/870.16, 340/539.13, 359.13, 309.16, 568, 681, 687, 340/870.07; 235/384, 381; 600/300; 128/903; 702/150; 700/12
See application file for complete search history.

(56) References Cited

U.S. PATENT DOCUMENTS

| | | | |
|---|---|---|---|
| 4,800,538 A | | 1/1989 | Passmore et al. |
| 5,852,590 A | * | 12/1998 | de la Huerga ................. 368/10 |
| 5,905,247 A | | 5/1999 | Ilén |
| 5,917,429 A | * | 6/1999 | Otis et al. ............... 340/870.31 |
| 6,294,999 B1 | * | 9/2001 | Yarin et al. ............... 340/573.1 |
| 6,471,645 B1 | * | 10/2002 | Warkentin et al. .......... 600/300 |
| 6,687,190 B2 | * | 2/2004 | Momich et al. ................ 368/10 |
| 6,897,788 B2 | * | 5/2005 | Khair et al. ........... 340/870.16 |
| 2002/0123672 A1 | * | 9/2002 | Christophersom et al. .. 600/300 |
| 2003/0004403 A1 | * | 1/2003 | Drinan et al. ............... 600/301 |
| 2003/0033032 A1 | * | 2/2003 | Lind et al. ..................... 700/52 |
| 2003/0036683 A1 | * | 2/2003 | Kehr et al. ................. 600/300 |

FOREIGN PATENT DOCUMENTS

| WO | WO 01/53922 A2 | 7/2001 |
|---|---|---|
| WO | WO02/087681 A2 | 7/2002 |

OTHER PUBLICATIONS

European Search Report of May 8, 2003, for EP patent application No. 03250577.8 filed Jan. 30, 2003, 5 pgs.

* cited by examiner

*Primary Examiner*—Jeffery Hofsass
*Assistant Examiner*—Sisay Yacob
(74) *Attorney, Agent, or Firm*—Banner & Witcoff, Ltd.

(57) ABSTRACT

The present invention concerns a data acquisition and transfer device comprising a sensor responsive to change of predetermined nature, and a transmitter for transmitting over the mobile phone network data concerning the occurrence of such a change to a receiver station. Such devices can be used in monitoring patients compliance when undergoing drug trials and can form part of a system which polls the device for changes and keeps a record of all transmissions.

11 Claims, 10 Drawing Sheets

EVENT DETECTION AND TRANSMISSION SYSTEM

CROSS-REFERENCE TO RELATED APPLICATIONS

This application claims priority benefit of European Patent Application Serial No. 03250577.8, filed Jan. 30, 2003, titled "EVENT DETECTION AND TRANSMISSION SYSTEM".

FIELD OF INVENTION

The present invention concerns a data acquisition and transfer system for transferring data via the mobile phone network. It is particularly but not exclusively concerned with the transfer of data from individuals to a central reception point and it is contemplated that the data may take many different forms. However, one important feature with which the present invention is concerned is that the major telecommunications operators and electronic suppliers are at present involved in the complex and difficult process of moving from the second generation of mobile phones to the third generation. As a result of this shift major companies are going to own increasingly under-utilised second generation digital networks and manufacturing capabilities for some time to come. Thus an aspect of the present invention is concerned with providing a range of opportunities which will enable these under-utilised facilities to remain revenue generating in a profitable manner.

One such opportunity lies in the field of drug testing. The process of testing new drugs in order to have them approved by the appropriate regulatory bodies can cost major drug firms up to a million dollars in lost revenue for each extra day needed to get approval.

One of the reasons it takes so long to get drugs approved is the length of time it takes to get sufficient good quality data out of the trials which have to be carried out. Doctors frequently mis-record data, and double-blind trials are expensive and take time to arrange. It is believed that schemes already exist to bypass the problems raised for example by doctors' handwriting and other vagaries in which test data is captured via the web. However errors still occur and the data is often inaccurate.

Thus in accordance with one aspect of the present invention data will be collected directly from the patient and from the receptacle from which the trial drug is dispensed.

It will, however, be appreciated that the basic inventive concept is applicable to a wide range of fields and is not necessarily limited to the concept of drug trials. Thus as will be apparent from the following description the inventive concept is applicable to monitoring the health of individuals who are not undergoing drug trials, locating or monitoring individuals for security purposes and also for carrying out regular checks on operating machinery.

BRIEF DESCRIPTION OF DRAWINGS

In order that the present invention may be more readily understood, the embodiments thereof will now be described by way of example and with reference to the accompanying drawings in which.

Figure 1:
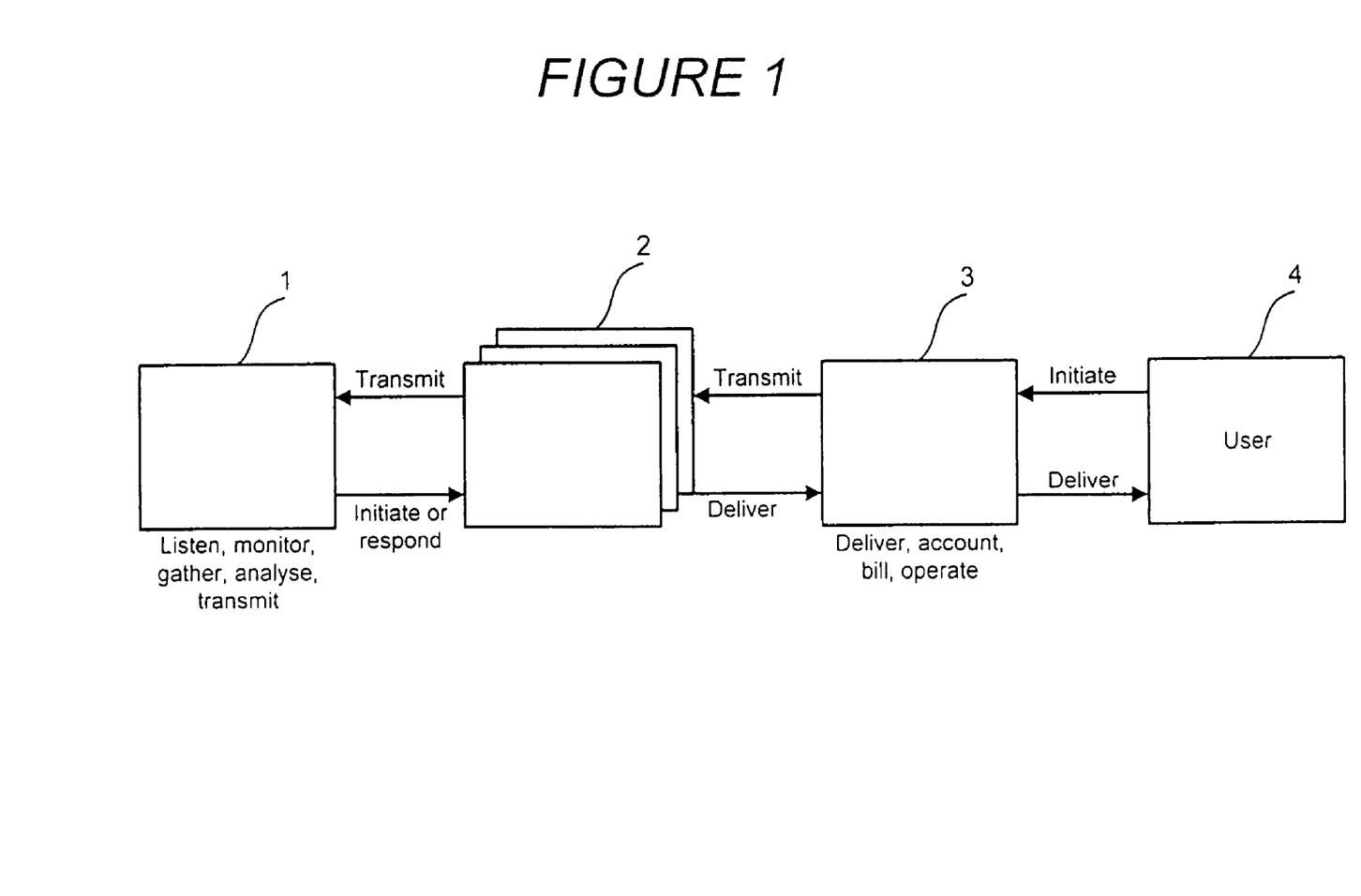
FIG. 1 is a schematic diagram of the overall system architecture.

Referring now to the drawings, FIG. 1 represents in a generic fashion a family of monitoring and transmitting devices which will be described in greater detail hereinafter. Block 1 represents a generic sensor device for obtaining data and for transmitting the acquired data. Block 2 represents the data telecommunications networks (and their operating companies) over which the data is transmitted to the device 1 so as to trigger a response to data which is transmitted from the device 1 either in response to a change in the circumstances of the device, to a signal initiated by an internal clock or in response to a request received to and from a processing centre shown at 3. Block 4 represents a user of the system for which the data, perhaps after analysis in block 3, is eventually returned. The directions of transmission of the data are shown by the headed arrows.

Figure 2:
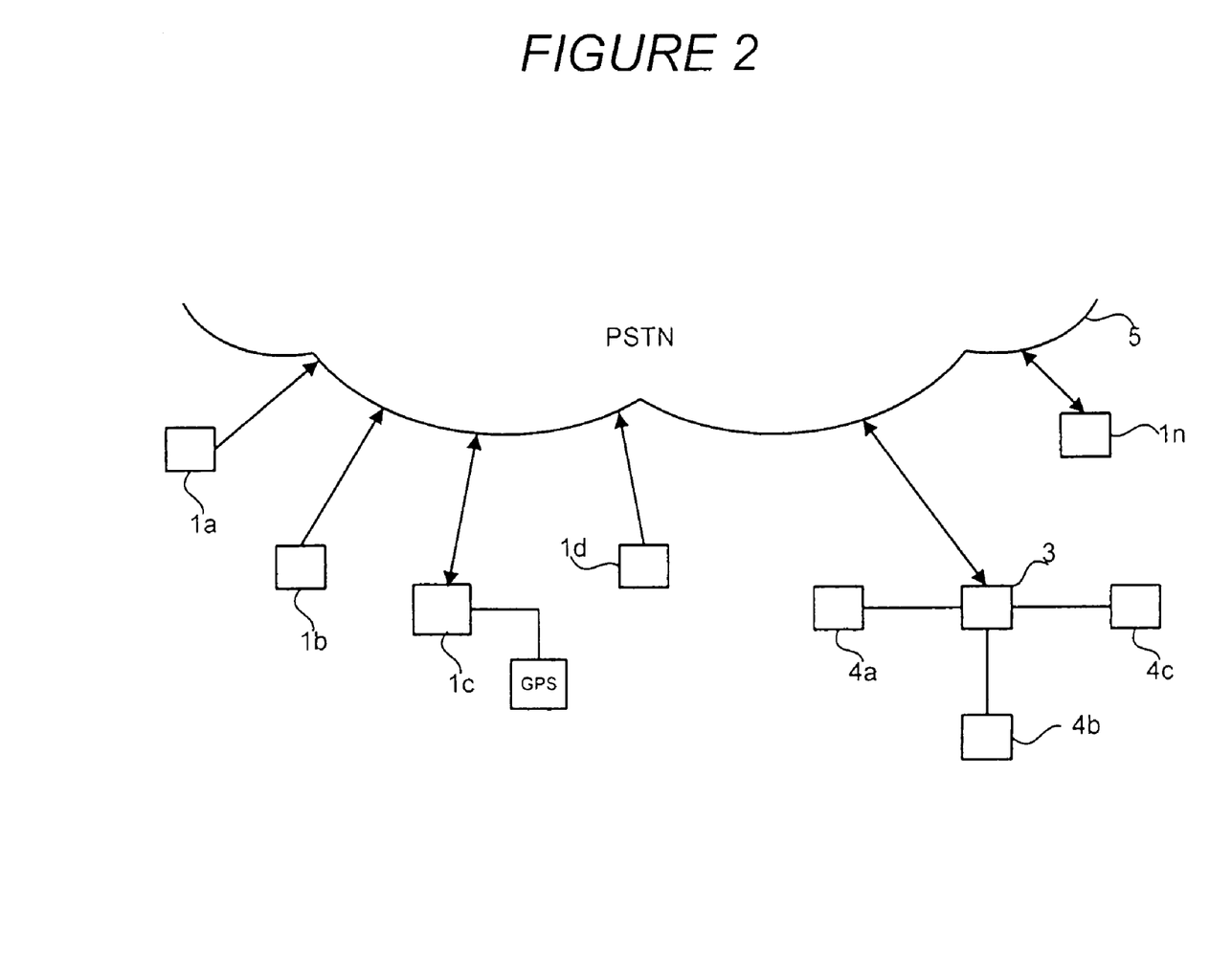
FIG. 2 is a diagram showing elements of the present invention in conjunction with the public services telephone network.

Turning now to FIG. 2 of the accompanying drawings, this shows a conventional representation of the public services telephone network at 5. Connected to the PSTN 5 are a number of blocks 1*a* . . . 1*n* each corresponding to block 1 of FIG. 1. As will be appreciated these devices need not be identical and may in fact have a number of different functions. It is for this reason that some of the devices are connected to the PSTN 5 by double headed arrows indicating that they are capable of both receiving and transmitting data to the centre 3 whilst other devices only have a single headed arrow indicating that they are only capable of sending data to the centre 3. As there are several different types of device 1, there may also be several different organisations each interested in acquiring data so that FIG. 2 shows three such organisations 4*a* . . . 4*c*.

Figure 3:
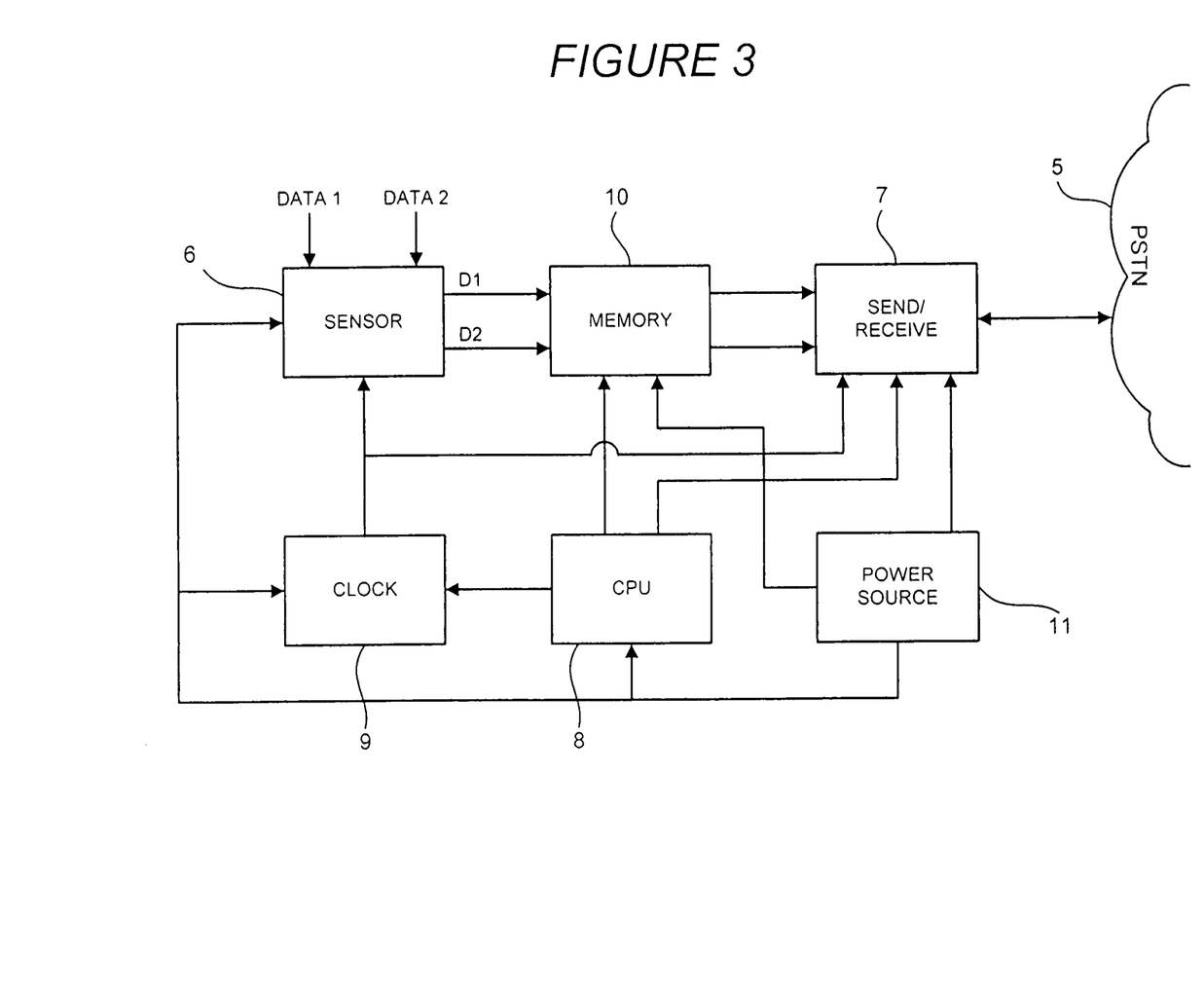
FIG. 3 is a block diagram of a sensor/transmitter.

Turning now to FIG. 3 of the accompanying drawings, this is a block diagram of circuitry which can be employed in the devices 1*a* . . . 1*n*. Thus the block diagram comprises a sensor 6 shown in the figure as having two data inputs, data 1 and data 2 and adapted to send data corresponding to the two inputs to a second generation transmit/receive circuit 7. The circuit 7 operates under the control of a microprocessor CPU unit 8 which also controls a clock 9. The clock reduces power consumption of the sensor by only switching the sensor on in response to appropriate commands from the CPU 8. Thus in several of its potential functions the device has a power saving sleep mode. Thus the sensor can sense data 1 and data 2 either simultaneously or at staggered intervals which need not be the same. Because of the possibility that the sensors may be required to operate over extended periods of time the question of power usage is of considerable importance and this feature will be described in greater detail hereinafter in conjunction with FIG. 10 of the accompanying drawings. The transmit/receive circuit 7, the CPU 8, and the clock 9 may all be formed as a microcircuit on a single chip. The circuit can include an optional memory 10 and also includes a power source 11 which can be any suitable small battery such as the lithium batteries used to power calculators and digital watches. It is of course entirely possible for the power source to include photocells so that electrical energy can be generated by ambient light.

It will be appreciated that the nature of the sensor has not been specified and it is of course possible for the sensor to have only a single data input or a plurality of data inputs greater than two in number in accordance with the functions of the sensor within the overall system.

Returning now to device 1a of FIG. 2.

It will be appreciated that the device shown in. FIG. 3 is essentially a generic one and that certain of the devices shown in FIG. 2 have only a one-way communication path with the PSTN 5 so that they cannot be interrogated by the centre 3. In these devices the send/receive circuit 7 need of course only have a send capability so that it can be simplified. Naturally if efficiencies of scale are present it may be simpler to have a send/receive capability in every device with the receive facility only being enabled in the appropriate circumstances.

One embodiment of a device such as 1a will now be described with regard to FIGS. 4 and 5 of the accompanying drawings. Thus device 1a is concerned with monitoring a drug testing program in which the patient has to take a regular dosage of the drug under test and in which a drug company is interested in the patient's response to this dosage. In this embodiment it is accordingly necessary for the drug company to know both when a pill is taken and the response by the patient to the taking of the drug. In its simplest form the device 1a a will merely indicate that the patient has opened the pill receptacle. On the opening of the receptacle, the sensor is intended to give an instruction to the transmit circuit to send a short text message to the processing centre 3 where the fact that the receptacle has been opened, and the timing of its opening, is logged for future analysis and transmission to the initial user, namely the drug company, for whom the data is intended.

Figure 4:
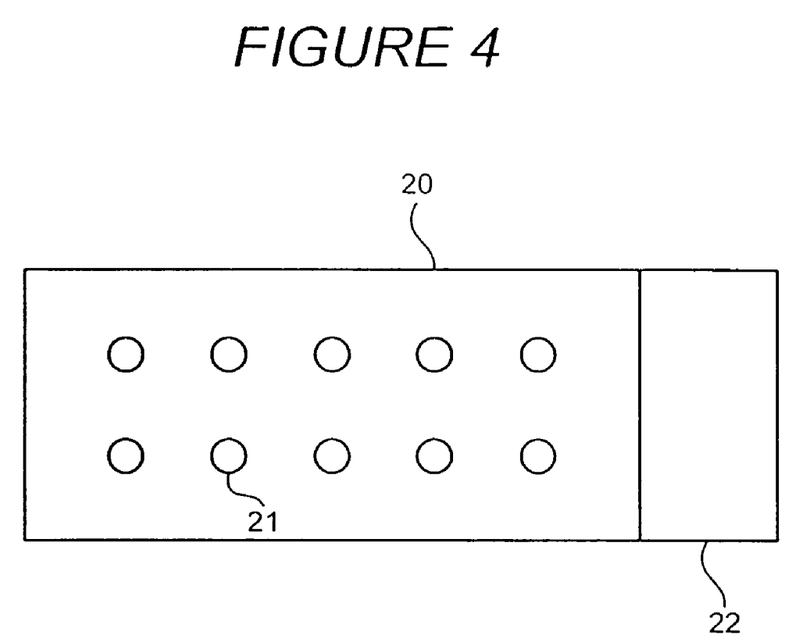
FIG. 4 is a plan view of a pill receptacle which can be used in the system shown in FIGS. 1 and 2.

FIG. 4 of the drawings shows a typical receptacle for pills in the form of a laminated strip 20 having an electro conductive metal foil surface provided with recesses 21 each holding a single pill. The sensor and its associated circuitry and power supply are located at 22. When the patient breaks the laminated foil to remove a pill, this is detected by the sensor which causes the send circuit 7, shown in FIG. 5, to send the appropriate message. In FIG. 5 the laminated foil is again shown at 20 and provides a conductive path between the power source 11 and the sensor 6 which path is changed each time the laminate is broken to enable the patient to remove a pill. Accordingly the sensor 6 can operate by detecting changes in the resistance or capacitance of the conductive foil. The foil and the various items of circuitry are mounted on a backing strip 22 of suitable material such as thick paper or cardboard which is relatively tougher than that of the foil so that a user will preferentially break the laminate to activate the sensor. Given that the device employs a microprocessor and associated memory it is possible to pre-program the device with a schedule so that if the schedule is not followed an alert message is transmitted to the centre 3.

In applications where the intervals between pills being taken are not critical to the safety of the patient, a more sophisticated embodiment of the present invention may be used. In one such embodiment, data will be transmitted to the centre 3 on the transmission of a polling request from the centre 3. In such a case the breaking of the foil might not cause the immediate transmission of a signal to the centre 3 but will merely cause the fact that the foil has been broken to be stored in memory. Accordingly, when a request is received the stored data will then be sent as before. In another variant information about the timing of each pill's removal can be stored in memory contained within the foil pack, and all such stored data may be transmitted in a single communications session, so that the battery power requirements of the foil pack, and thus its size and weight, are reduced.

There will now be described a more sophisticated variant of the device just described with reference to FIGS. 4 and 5. As already mentioned it may well be that the drug company instigating the tests will require further information in addition to the fact that a patient has been taking his/her pills at the appropriate times and logging the times at which the pills were taken. Thus it is entirely possible for the drug company to wish to be able to monitor changes in the patient's condition when undergoing the drug regime. In such a situation it may be necessary for the patient to be provided with two sensing and transmitting devices. One device could be similar to the device just described with regard to FIGS. 4 and 5 whilst the other device could be a more sophisticated variant of this device which is attached to the patient and which monitors factors relevant to the patient's state of health. Such factors could be blood pressure, temperature, heart rate, skin pH and perspiration rate etc. and will of course depend on the nature of the drug being tested. Accordingly in this variant of the present invention the sensor 6 will accept a number of different inputs so that the required information can eventually be transmitted to the main centre 3. Additionally in order to conserve power the sensor may only be activated in response to a request received at the circuit 7 for stored information to be sent as text messages back to the centre 3. One way of ensuring that the data is relevant would be to time the polling request appropriately in response to data already transmitted with regard to the timing of the patient's taking of the drug. In this scenario it is assumed that there is no direct linkage between the sensor monitoring the patient's condition and the sensor monitoring the taking of the drugs. However, in another variant one or other of the devices could send its stored data to be appended to the data stored in the other device so that on interrogation from the centre 3 all the appropriate data is transmitted at the same time.

The device associated directly with the patient could be in the form of a bracelet worn by the patient or in the form of a patch such as one or more electrodes attached directly to the patient's skin by suitable adhesives or taping and worn under the patient's clothing.

Figure 5:
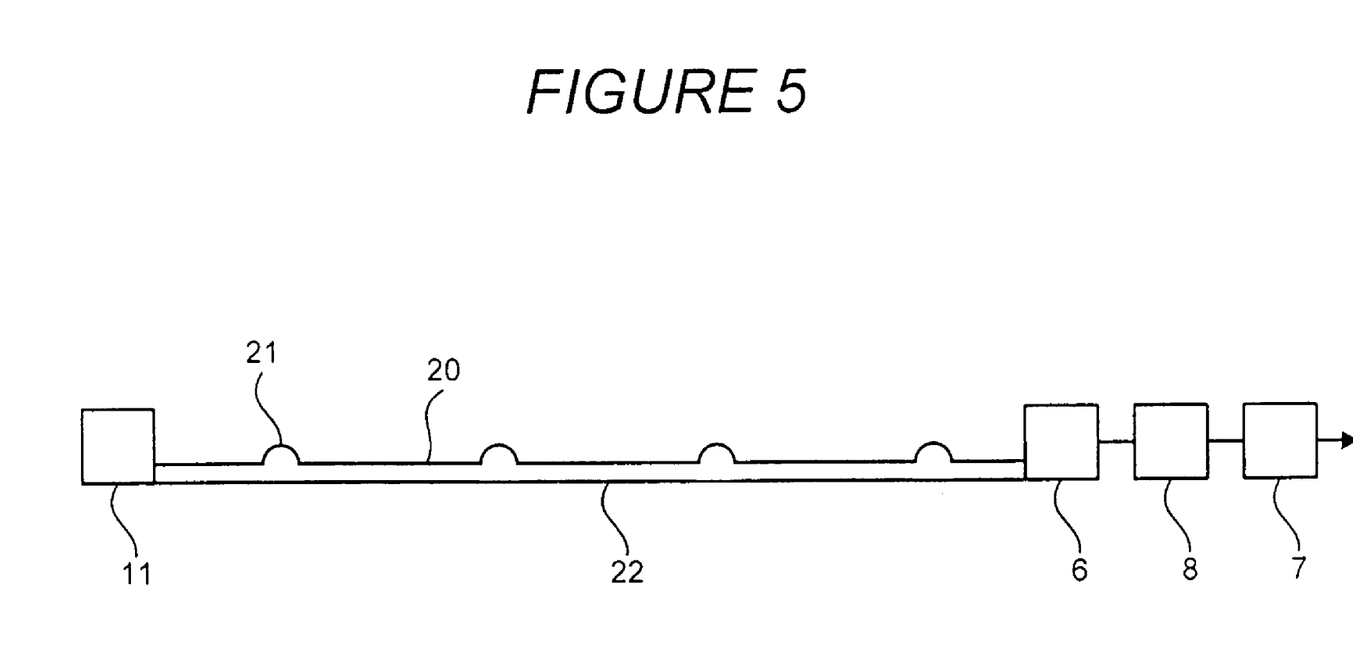
FIG. 5 is a block diagram of the active components of FIG. 4.
Figure 6:
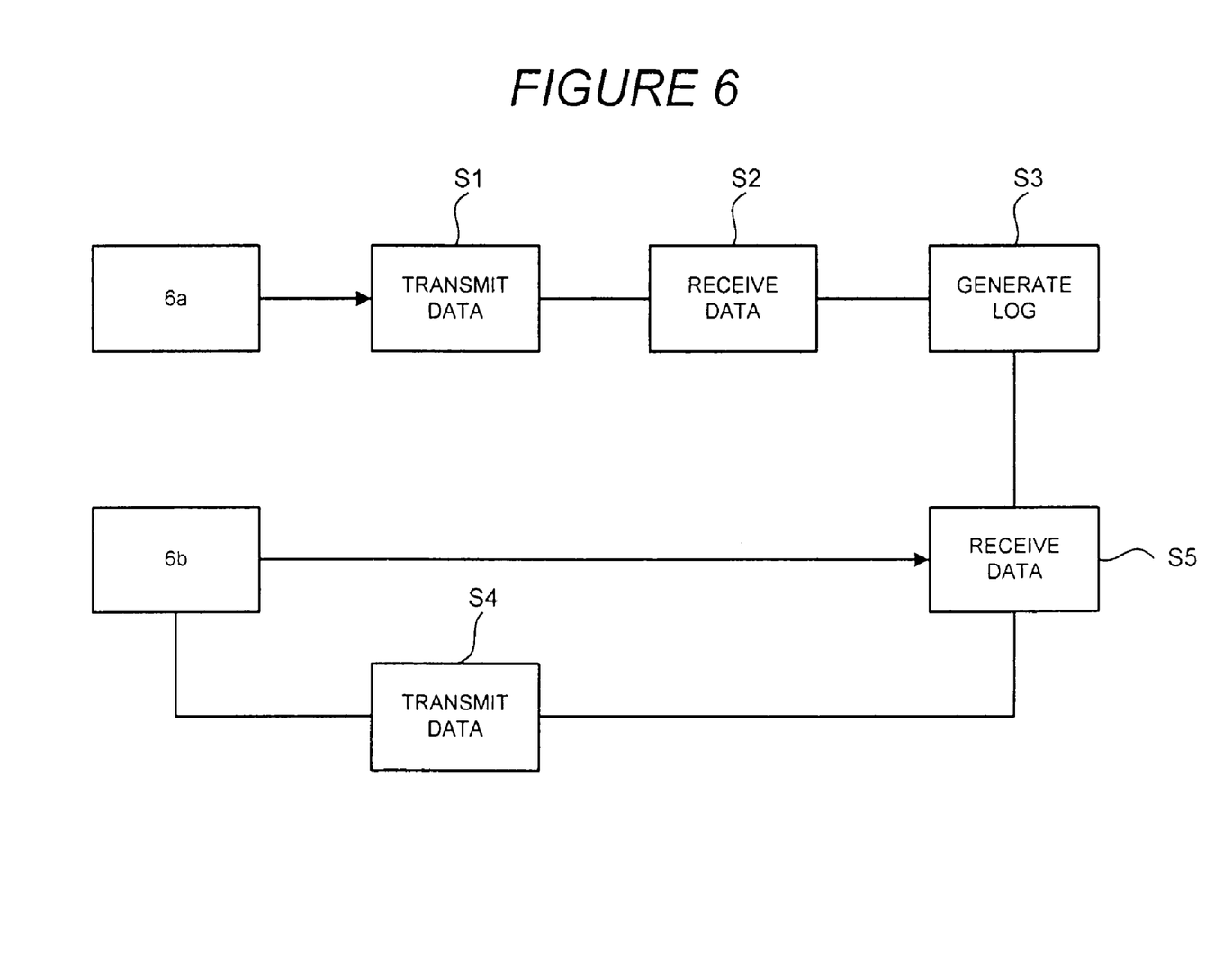
FIGS. 6 and 7 are flow charts showing modes of operation of the device of FIG. 5.
Figure 7:
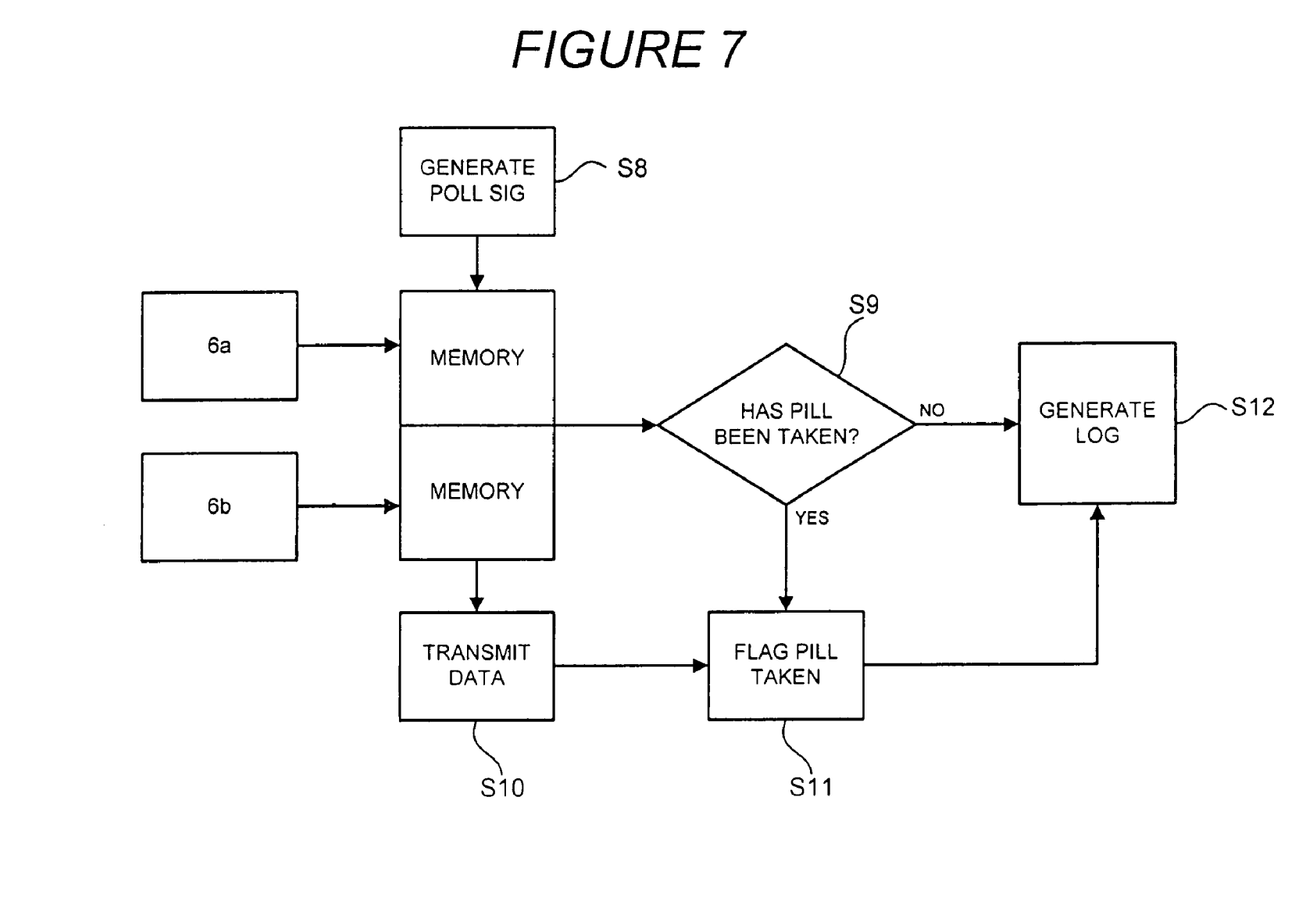

The flow diagrams of FIGS. 6 and 7 show alternative ways in which the generated data can be accessed by the centre 3. In these flow diagrams 6a represents the sensor 6 shown in FIGS. 4 and 5 and 6b represents a similar sensor but monitoring health characteristics of the patient involved. It will be appreciated that both of these sensors are similar to the one described with reference to FIG. 3.

In the flow diagram of FIG. 6 it is assumed that the sensor 6a operates in its normal manner and when a pill is taken transmits this fact at step S1 to the centre 3 where it is received at step S2. At step S3 a computer (not shown) at centre generates a log indicating that a particular patient has taken a particular pill at a particular time. In step S4 the centre 3 sends a request to interrogate the sensor 6b and to request the latter to transmit in step S5 the data that it has acquired back to the centre 3 so that this data can be added to the log generated at step S3. Naturally the data accessed in the transmit request step S4 can also include previous data which has been stored by the sensor 6b at appropriate intervals after the last time it was polled by the centre 3.

In the flow diagram of FIG. 7 an alternative scenario is shown in which the output of sensor 6a in response to the removal of a pill is stored in memory at step S8 together with data from sensor 6*b* for subsequent transmission. In step S8 the centre 3 generates a poll signal to interrogate the stored data.

In response to this interrogation step a step S9 makes the decision as to whether or not one or more pills have been taken since the last poll of the device. This information would of course be of importance to the company making the drug trial. Whether or not a pill has been taken data concerning the patients condition is transmitted in step S10 and the fact that a pill has been taken is flagged in step S11. If a pill has not been taken this information is also supplied to step S12 where a log of the available data is generated for subsequent use.

It will be appreciated that the embodiment of FIG. 7 could be changed in a relatively simple manner by keeping the data separate in two streams in which each memory 10 of each sensor device is interrogated by the centre 1 with each sensor device sending its relevant data independently of the other to generate the final log at the centre 1.

It will be appreciated that in the system just described the quality of data gathered is likely to be much more accurate than similar data gathered by a doctor or even from a patients own records and it would also be gathered much faster. The advantage for this for the drug company carrying out the tests is clear in that there will be reduced time delay before a successful drug can be marketed. Additionally for the telecommunication network operator the advantage is higher utilisation of their network, but with limited life span contract thus for a drug testing program each sensor might be required to be able to operate over a matter of a few weeks or months. For the electronic suppliers there will be the corresponding advantage of the opportunity to get more utilisation out of their 2g second generation cellular telephone chip set production capabilities. However, it must be appreciated that exactly the same concept may be applied when inevitable progress means a move from third generation chip sets to fourth generation chip sets and so on.

Figure 8:
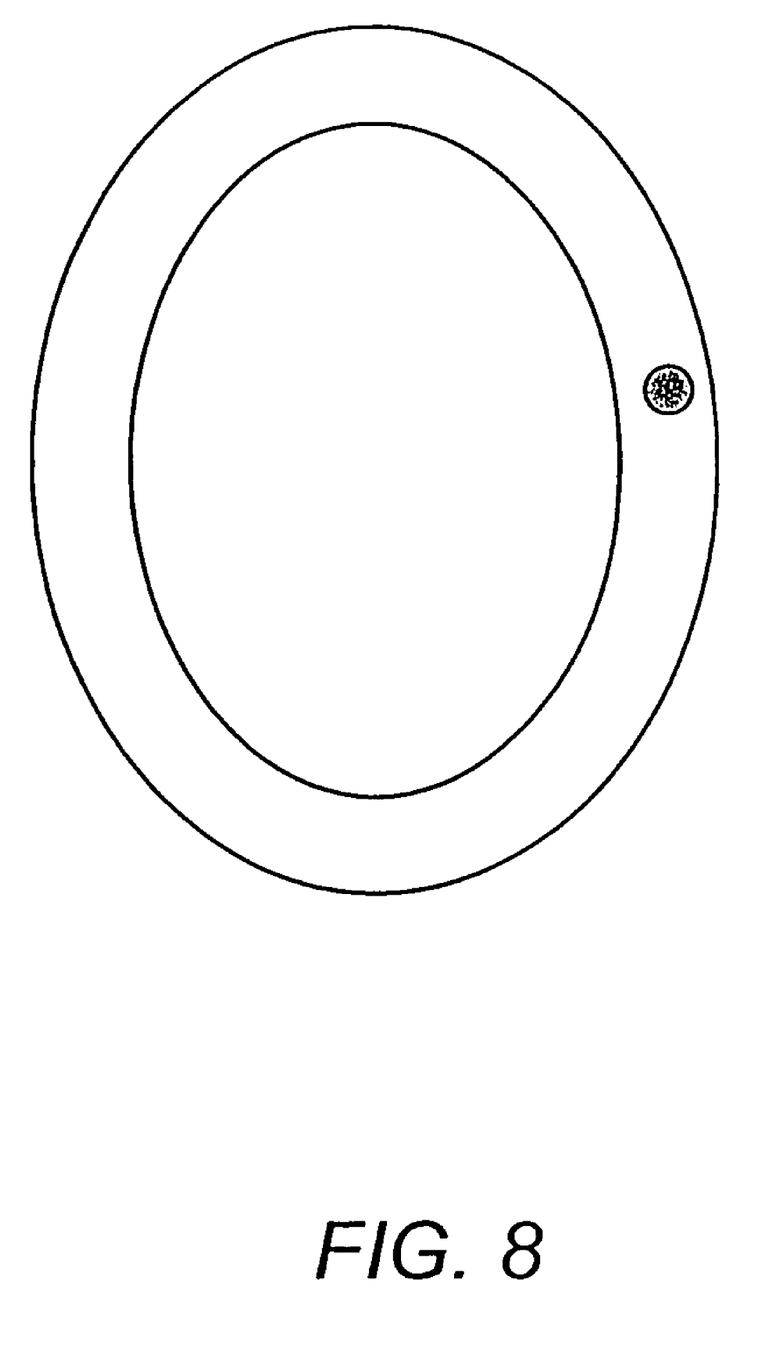
FIG. 8 shows another form of pill receptacle.

It must be appreciated that the receptacle for pills disclosed in FIGS. 4 and 5 can take other forms. Thus FIG. 8 shows the receptacle in the form of a standard pill bottle 30. In such a case the sensor 6 will merely record for transmission the removal of the led of the bottle.

Figure 9:
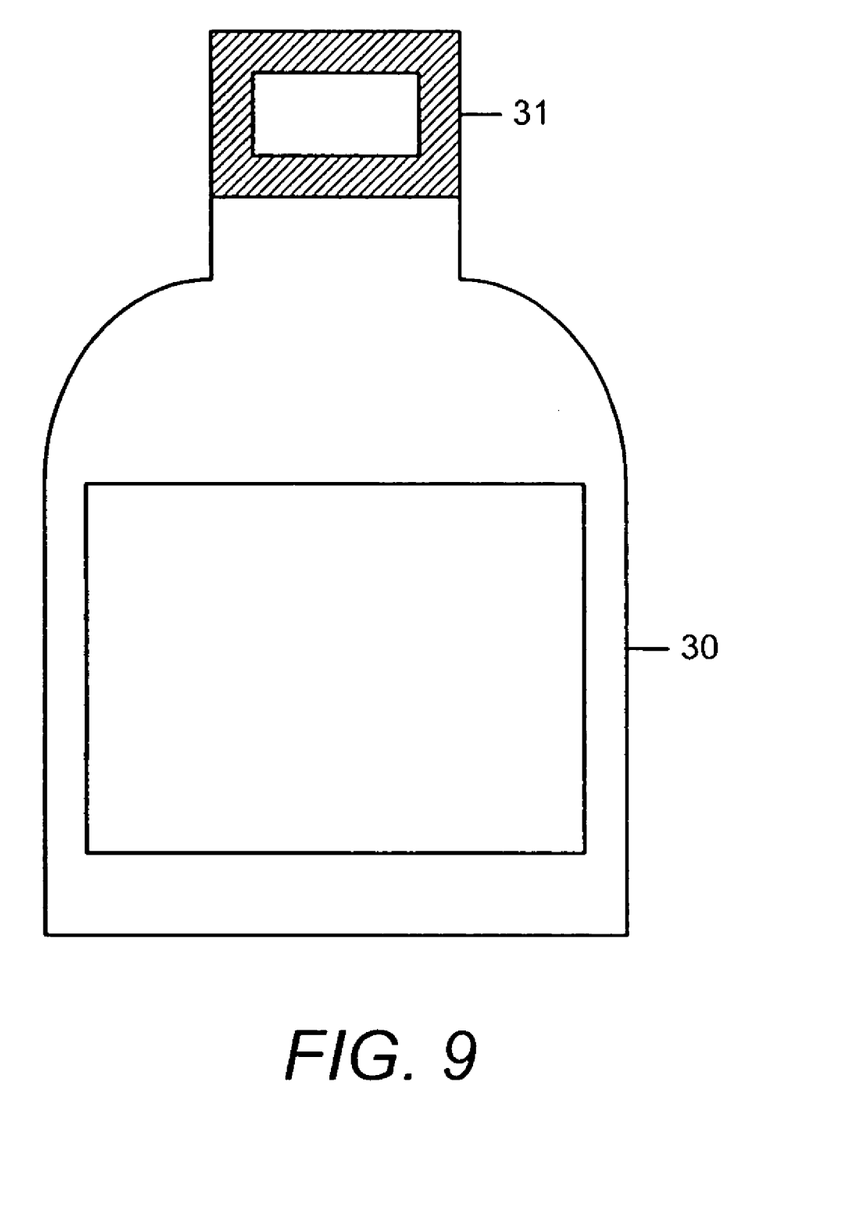
FIG. 9 shows a sensor bracelet.

FIG. 9 shows a bracelet 40 which can be worn by a user, in order to detect variations in the user's bodily functions.

As already mentioned the basic sensor configuration shown in FIG. 3 has the potential to carry out a wide range of functions. Thus the device shown at 1*b* in FIG. 2 could be utilised to detect the possibility of impending heart attacks in a patient. In this case, the sensor 6 has appropriate sensors and embedded software that detect heart beat patterns that are known to be precursors of a heart attack. When these are detected by the CPU the transmit section will be enabled to send an appropriate message to the centre 3 so that emergency services could be alerted. It is of course possible also to alert the wearer with the risk that the shock might advance the heart attack.

In an exactly equivalent manner the sensor just described could be associated with machinery rather than with individual humans so as to detect actual or imminent failure and alert owners or maintenance companies. The sensors can also provide useful data to manufacturers about the conditions under which a product fails.

Sensor 1*c* in FIG. 2 is shown as having a GPS capability and in this variant of the invention the sensor 6 is a motion location sensor and the send/receive circuit 7 can be simplified so that it is a single-use message sender. Such a device can be attached to valuable items so that if they are moved the police will be alerted. Combining this feature with the GPS capability the device will also be able to tell the police where the article is.

As is apparent from the foregoing description one of the advantages of the centre 3 is that it can operate on behalf of a number of clients and that it will also generate a substantial amount of secondary data.

In all of the variants described above the question of maintaining a sufficient power supply for the sensors and their associated send/receive circuits is of considerable importance. In order to conserve power each sensor may have a sleep mode in which there is minimal power consumption in such a case the sensor might only respond to a polling signal from the centre 3 and be quiescent until the polling signal has been received.

Figure 10:
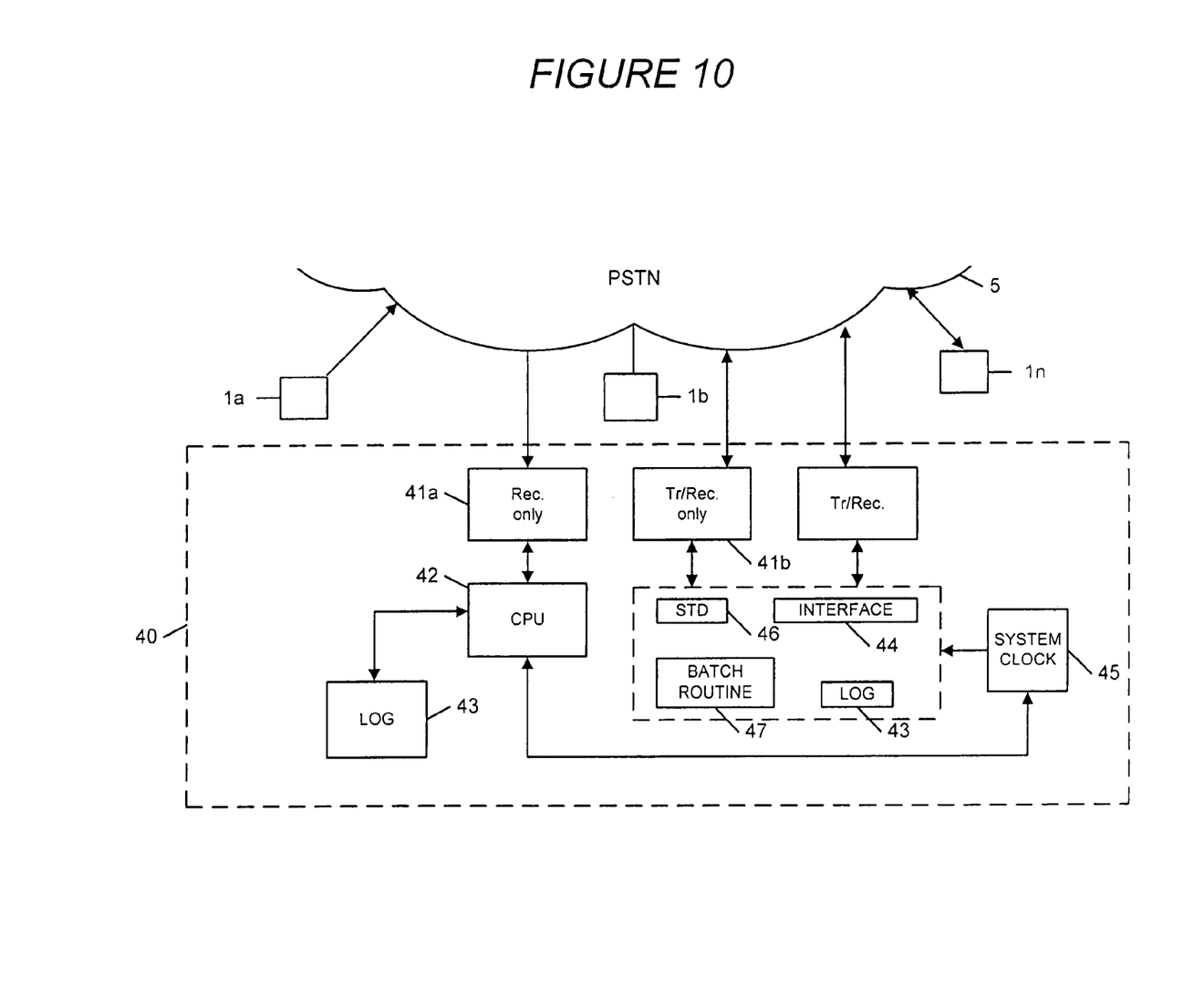
FIG. 10 is a block diagram of data reception and polling terminal incorporating the present invention.

Turning now to FIG. 10 of the accompanying drawings this shows in greater detail a data reception and polling terminal 40 corresponding to the centre 3 shown in FIG. 2.

FIG. 10 again shows the PSTN network at 5 and sensor devices 1*a* . . . 1*n*. As before some of these devices have only a transmit capability and others have a receive/transmit capability.

In the centre of polling terminal 40 blocks 41*a*, 41*b* and 41*c* represent receive terminals for receiving data signals from devices similar to send only device 1*a* or for both sending data to and receiving data from sensor devices such as device 1*n*. Thus terminal 41*a* represents a receive-only terminal, whilst terminals 41*b* and 41*c* are transmit/receive terminals. Each terminal is capable of at least receiving data from a large number of sensor devices, and some terminals can also transmit to a large number of sensor devices. Associated with each terminal is an electronic processor. Terminal 41*a* is shown connected to a processor 42 whilst terminals 41*b*, 41*c* are shown connected to a data processing system 44. Processor 42 on receipt of data from a sensor devise is programmed to recognise the source of the data and to log the data, including time of receipt, in an appropriate storage area 43.

Data processing system 44 is also capable of generating outgoing data such as polling calls and is also programmed to store in appropriate files details of all outgoing and incoming data as required by a user of the system. As already discussed power conservation is an important factor in the operation of the various sensors. Thus it will be seen that polling terminal 40 also includes a system clock which can be of any suitable type. Each processor can have its own clock or, as shown a single clock can be used. Data processing system 44 also includes a storage area 46 storing Sensor Timing Data, namely the time at which each sensor which is to be polled in synchronism with that sensors clock switching the sensor on and in addition, if there are passive sensors, the times at which data is expected to be received from the sensors. The data processing system 44 also includes a stored set of batch routines indicated at 47 in order to control the polling of target sensors at appropriate times as set by the STD file 46. The batching routine can also flag if a non-polled sensor has been quiescent for too long a period in response to data stored on the same file area. Provided that each sensor clock 9 is in nominal synchronism with the system clock or its associated clock then the combination of the synchronised clocks, the STD file and the Batch routine will ensure that each device to be polled can remain in a very lower power. Mode with only its clock operational and its memory contents refreshed except when data is required. Naturally the polling times will vary with polling intervals for security sensors being shorter than those, for example, drug testing.

The invention claimed is:

1. A data receiver station for use with a data acquisition and transfer device, the data acquisition and transfer device having first and second sensors each responsive to a change of a predetermined nature and a transmitter for transmitting over a mobile phone network data concerning an occurrence of each change to the data receiver station, wherein the data receiver station comprises:

a transmitter configured to send a first polling signal over the mobile phone network to the data acquisition and transfer device requesting data associated with a change detected by the first sensor, and a second polling signal over the mobile phone network to the data acquisition and transfer device requesting data associated with a change detected by the second sensor;

a receiver configured to receive the data associated with the first and second sensors over the mobile phone network; and a controller configured to determine a time for sending the second polling signal depending upon a content of the first data and to control the transmitter to send the second polling signal at the determined time.

2. The data receiver station of claim 1, wherein the content of the first data includes an indication of when the first sensor detected the change, and wherein the controller is configured to determine the time for sending the second polling signal depending upon when the first sensor detected the change.

3. A data receiver station, comprising:

a transmitter configured to transmit a first polling signal at a first time and a second polling signal at a second time;

a receiver configured to receive data sent in response to and after the first polling signal; and a controller coupled to the transmitter and the receiver and configured to determine the second time depending upon a content of the data received by the receiver and to control the transmitter to send the second polling signal at the second time.

4. The data receiver station of claim 3, wherein the content of the data includes an indication of when a sensor detected a change in a physical characteristic, and wherein the controller is configured to determine the time for sending the second polling signal depending upon when the sensor detected the change.

5. The data receiver station of claim 3, wherein the transmitter is configured to transmit the first polling signal over a phone network and the receiver is configured to receive the data over the phone network.

6. The data receiver station of claim 3, further including a memory, wherein the controller is further configured to determine a time of receipt of the data and to store both the content of the data and the time of receipt of the data in the memory.

7. A data acquisition system, comprising:

a data receiver station, comprising:

a first transmitter configured to transmit over a network a first polling signal at a first time and a second polling signal at a second time, a first receiver configured to receive first data and second data, and a controller coupled to the first transmitter and the first receiver and configured to determine the second time depending upon a content of the first data received by the first receiver and to control the first transmitter to send the second polling signal at the second time; and a data acquisition device, comprising:

a second receiver configured to receive over the network the first and second polling signals, a first sensor configured to sense a first physical characteristic, a second sensor configured to sense a second physical characteristic, and a second transmitter configured to transmit the first and second data, wherein the data acquisition device is configured to generate the first data based on the first physical characteristic as sensed by the first sensor and to generate the second data based on the second physical characteristic as sensed by the second sensor, and is further configured to transmit by the second transmitter the first data in response to the second receiver receiving the first polling signal and the second data in response to the second receiver receiving the second polling signal.

8. The data acquisition system of claim 7, wherein the content of the first data includes an indication of when the first sensor detected the first physical characteristic, and wherein the controller is configured to determine the time for sending the second polling signal depending upon when the first sensor detected the first physical characteristic.

9. The data acquisition system of claim 7, wherein the network is a phone network.

10. The data acquisition device of claim 7, further including a memory, wherein the controller is further configured to determine a time of receipt of the first data and to store both the content of the first data and the time of receipt of the first data in the memory.

11. The data acquisition device of claim 7, wherein the first and second physical characteristics are changes in physical characteristics.

* * * * *

UNITED STATES PATENT AND TRADEMARK OFFICE
CERTIFICATE OF CORRECTION

PATENT NO.        : 7,242,318 B2                                              Page 1 of 1
APPLICATION NO.   : 10/769206
DATED             : July 10, 2007
INVENTOR(S)       : Alan Harris It is certified that error appears in the above-identified patent and that said Letters Patent is hereby corrected as shown below:

On the Cover Page, Foreign Application Priority Data, Section (30):
  Please delete "03250577" and insert --03250577.8--

Signed and Sealed this

Eighteenth Day of March, 2008

JON W. DUDAS
*Director of the United States Patent and Trademark Office*